United States Patent [19]

Mak et al.

[11] Patent Number: 5,616,491
[45] Date of Patent: Apr. 1, 1997

[54] KNOCKOUT MICE

[75] Inventors: Tak W. Mak, Toronto, Canada; Craig B. Thompson, 1375 E. 57th St., Chicago, Ill. 60637

[73] Assignees: Ontario Cancer Institute, Toronto, Canada; Craig B. Thompson, Chicago, Ill.

[21] Appl. No.: 528,363

[22] Filed: Sep. 14, 1995

Related U.S. Application Data

[63] Continuation of Ser. No. 67,767, May 26, 1993, abandoned.

[51] Int. Cl.$^6$ .............................. C12N 5/00; C12N 15/00
[52] U.S. Cl. .................. 435/354; 435/320.1; 435/172.3; 435/355; 536/23.1; 800/2; 800/DIG. 1; 935/22; 935/70
[58] Field of Search .............................. 435/240.2, 320.1, 435/172.3; 536/23.1, 23.5; 800/2, DIG. 1; 935/22, 70

[56] References Cited

FOREIGN PATENT DOCUMENTS

WO92/22645  12/1992  WIPO.
WO93/05817  4/1993  WIPO.

OTHER PUBLICATIONS

Allan Bradley and Elizabeth Robertson, Embryo–Derived Stem Cells: A Tool for Elucidating the Developmental Genetics of the Mouse, *Current Topics in Developmental Biology*, vol. 20, pp. 357–371.

Charbonneau et al., The leukocyte common antigen (CD45): A putative receptor–linked protein tyrosine phosphatase *Proc. Natl. Acad. Sci.*, vol. 85, pp. 7182–7186, Oct. 1988.

Ferrick et al., Transgenic Mice as an in vivo Model for Self–Reactivity, *Immunological Reviews*, No. 118, pp. 257–283, 1990.

Wai–Ping Fung–Leung and Tak Mak, Embryonic stem cells and homologous recombination, *Current Opinion in Immunology*, 4: 189–194, 1992.

Fung–Leung et al., Immune Response against Lymphocytic Choriomeningitis Virus Infection in Mice without CD8 Expression, *J. Exp. Med.*, 174: 1425–1429, 1991.

Fung–Leung et al., CD8 Is Needed for Development of Cytotoxic T Cells but Not Helper T Cells, *Cell*, vol. 65, 443–449, 1991.

Johnson et al., Sequence Conservation in Potential Regulatory Regions of the Mouse and Human Leukocyte Common Antigen Gene, *The Journal of Biological Chemistry*, vol. 264, No. 11, pp. 6220–6229, 1989.

Joyner et al., Production of a mutation in mouse En–2 gene by homologous recombination in embryonic stem cells, *Nature*, vol. 338, pp. 153–156, 1989.

Kishihara et al., Normal B Lymphocyte Development but Impaired T Cell Maturation in CD45–Exon6 Protein Tyrosine Phosphatase–Deficient Mice, *Cell*, vol. 74, 143–156, Jul., 1993.

Koretzky et al., Tyrosine phosphatase CD45 is required for T–cell antigen receptor and CD2–mediated activation of a protein tyrosine kinase and interleukin 2 production, *Proc. Natl. Acad. Sci.*, vol. 88, pp. 2037–2041, 1991.

Lee et al., The Genomic Organization of the CD28 Gene, *The Journal of Immunology*, vol. 145, 344–352, 1990.

Li et al., Human suppressor T cell clones lack CD28, *Eur. J. Immunol.*, 20: 1281–1288, 1990.

Peter S. Linsley and Jeffrey A. Ledbetter, The Role of the CD28 Receptor During T Cell Reseponses to Antigen, *Annu. Rev. Immunol.*, 11: 191–212, 1993.

Love et al., T Cell Development in Mice That Lack the $\xi$ Chain of the T Cell Antigen Receptor Complex, *Science*, vol. 261 pp. 918–921, Aug., 1993.

Tak Mak et al., Generation of Mutant Mice Lacking Surface Expression of CD4 or CD8 By Gene Targeting, *Journal of Autoimmunity*, 5:55–59, 1992.

Molina et al., Peripheral T Cells in Mice Lacking p56lck Do Not Express Significant Antiviral Effector Functions1, *The Jouranl of Immunology*, vol. 151, 699–706, No. 2, Jul. 1993.

Molina et al., Profound block in thymocyte development in mice lacking p56lck, *Nature*, vol. 357, 161–164, 1992.

Penninger et al., Requirement for Tyrosine Kinase p56lck for Thymic Development of Transgenic $\gamma\delta$T Cells, *Science* vol. 260, 358–361, Apr., 1993.

Pfeffer et al., Mice Deficient for the 55 kd Tumor Necrosis Factor Receptor Are Resistant to Endotoxic Shock, yet Succumb to L. monocytogenes Infection, *Cell.*, vol. 73, 457–467, May, 1993.

Pingel and Thomas, Evidence That the Leukocyte–Common Antigen Is Required for Antigen–Induced T Lymphocyte Proliferation, *Cell*, vol. 58, 1055–1065, 1989.

Rahemtulla et al., Targeted disruption of the murine CD4 gene in the germ–line by homologous recombination, *INSERM*, vol. 219, 287–289, 1991.

Rahemtulla et al., Normal development and function of CD8+ cells but markedly decreased helper cell activity in mice lacking CD4, *Nature*, vol. 353, 180–184, 1991.

Schilham et al., Alloreactive cytotoxic T cells can develop and function in mice lacking both CD4 and CD8, *Eur. J. Immunol.*, 23: 1299–1304, 1993.

Shahinian et al., Differential T Cell Costimulatory Requirements in CD28–Deficient Mice, *Science*, vol. 261, pp. 609–612, Jul., 1993.

Thomas and Capecchi, Site–Directed Mutagenesis by Gene Targeting in Mouse Embryo–Derived Stem Cells, *Cell*, vol. 51, pp. 503–512, 1987.

Thompson et al., Germ Line Transmission and Expression of a Corrected HPRT Gene Produced by Gene Tareting in Embryonic Stem Cells, *Cell*, vol. 56, 313–321, 1989.

Tonks et al., Demonstration That the Leukocyte Common Antigen CD45 is a Protein Tyrosine Phosphatase, *Biochemistry*, vol. 27, No. 24, pp. 8695–8701, 1988.

Wallace et al., CD45RA and CD45RBhigh Expression Induced by Thymic Selection Events, *J. Exp. Med.*, vol. 176, 1657–1663, 1992.

Weaver et al., CD8+ T–Cell Clones Deficient In the Expression of the CD45 Protein Tyrosine Phosphatase Have Impaired Responses to T–CellReceptor Stimuli, *Molecular and Cellular Biology*, vol. 11, No. 9, pp. 4415–4422, 1991.

*Primary Examiner*—Jasemine C. Chambers
*Attorney, Agent, or Firm*—Nancy A. Oleski

[57] ABSTRACT

Mice lacking expression of CD28 or particular CD45 isoforms in certain cells of the immune system are provided. Also provided are methods of using these mice.

3 Claims, 6 Drawing Sheets

KNOCKOUT MICE

This application is a continuation of U.S. Ser. No. 08/067,767 filed 26 May 1993, now abandoned.

FIELD OF THE INVENTION

This invention relates to mammals in which the expression of one or more genes has been suppressed. More specifically, the invention concerns insertion of an exogenous DNA construct into the genomic DNA of mammals thereby producing transgenic mammals with decreased or completely suppressed expression of an endogenous gene or genes.

DESCRIPTION OF RELATED ART

The immune system of mammals is comprised of many specialized cells that act together in a highly complex and orchestrated manner to protect the mammal from invading pathogens, toxins, and other foreign substances.

Cells responsible for the specificity of the immune system are referred to as lymphocytes. Lymphocytes are a class of white blood cells. Two important classes of lymphocytes are T cells and B cells. T cells develop in the thymus, and are responsible for cell mediated immunity. There are many types of specialized T cells, such as for example, helper T cells (which enhance the activity of other types of white blood cells), suppressor T cells (which suppress the activity of other white blood cells), and cytotoxic T cells (which kill cells). B cells develop in the bone marrow and exert their effect by producing and secreting antibodies.

Many disorders of the immune system exist, and new disorders are continually identified. One type of commonly occurring immune disorder is the hyperactive immune system. Here, certain factors induce particular cell types in the immune system to become activated when they should not be.

Another type of immune disorder is autoimmunity. This disorder is characterized by the immune system mounting an immune response against the mammal's own tissues.

Several proteins and other molecules have been identified as having key functions in regulating the immune system response of mammals. Two such proteins are CD28 and CD45.

CD28 receptor, also known as CD28, is a homodimer of molecular weight about 44 kilodaltons (kD). CD 28 is expressed at different levels on the cell surface of various T cells, and has a molecular structure similar to receptors of the immunoglobulin supergene family. CD28 appears to be involved in regulation of T cell activation, and ultimately seems to exert this effect by regulating T cell cytokine gene expression via tyrosine phosphorylation of certain intracellular substrates such as certain phospholipases. (see Linsley et al., *Ann. Rev. Immunol.*, 11:191–212 [1993]).

Another protein that is important in immune system regulation is the cell surface receptor molecule known as CD45 receptor or CD45. This molecule is expressed on the surface of many types of hematopoietic cells, including for example B cells and certain T cells. The gene encoding CD45 undergoes alternative splicing. CD45 has 34 exons (Johnson et al., *J. Biol. Chem.*, 264:6220–6229 [1989]). As a result, there are multiple isoforms of CD45. Different isoforms are expressed on different cells, but one cell type may express more than one isoform (Thomas, *Ann. Rev. Immunol.*, 7:339–369 [1989]). CD45 has a molecular weight of between about 180 kD and 235 kD, depending on the isoform. CD45 is a protein tyrosine phosphatase and is involved in cell signaling (Charbonneau et al., *Proc. Natl. Acad. Sci USA* 85:7182– 7186 [1988]; Tonks et al., *Biochem.*, 27:8695–8701 [1988]).

Murine T cell clones lacking expression of CD45 have been generated by chemical mutagenesis (Pingel et al., *Cell*, 58:1055–1065 [1989]; Weaver et al., *Mol. Cell. Biol.*, 11:4415–4422 [1991]). These cells failed to become activated (i.e., to proliferate) in response to certain compounds that normally serve as activation signals. The cells had other impaired functions as well such as decreased cytokine production.

A mutant human T cell leukemia cell line with suppressed CD45 expression has been generated using gamma irradiation (Koretzky et al., *Proc. Natl. Acad. Sci. USA*, 88:2037–2041 [1991]). Among other impaired functions, this cell line was shown to lack the ability to activate a T cell receptor associated tyrosine kinase.

While the use of isolated cell lines is helpful in understanding the role of various proteins on immune system regulation, more complete information can be obtained by studying the effects of these proteins directly in a mammal (i.e., an in vivo system). To this end, various mammals have been produced that have altered levels of expression of certain genes. One class of these mammals are the so called transgenic mammals. These mammals have a novel gene or genes introduced into their genome. Another class of these mammals is the so called knockout mammals, wherein expression of an endogenous gene has been suppressed through genetic manipulation.

A variety of transgenic mammals have been developed. For example, U.S. Pat. No. 4,736,866 issued 12 April 1988 describes a mouse containing a transgene encoding an oncogene.

U.S. Pat. No. 5,175,384, issued 29 December 1992, describes a transgenic mouse deficient in mature T cells.

U.S. Pat. No. 5,175,383, issued 29 December 1992, describes a mouse with a transgene encoding a gene in the int-2/FGF family. This gene promotes benign prostatic hyperplasia.

U.S. Pat. No. 5,175,385, issued 29 December 1992, describes a transgenic mouse with enhanced resistance to certain viruses.

PCT patent application No. WO 92/22645, published 23 December 1992, describes a transgenic mouse deficient in certain lymphoid cell types.

Preparation of a knockout mammal requires first introducing a nucleic acid construct that will be used to suppress expression of a particular gene into an undifferentiated cell type termed an embryonic stem cell. This cell is then injected into a mammalian embryo, where it hopefully will be integrated into the developing embryo. The embryo is then implanted into a foster mother for the duration of gestation.

Pfeffer et al. (*Cell*, 73:457–467 [1993]) describe mice in which the gene encoding the tumor necrosis factor receptor p55 has been suppressed. The mice showed a decreased response to tumor necrosis factor signaling.

Fung-Leung et al. (*Cell*, 65:443–449 [1991]; *J. Exp. Med.*, 174:1425–1429 [1991]) describe knockout mice lacking expression of the gene encoding CD8. These mice were found to have a decreased level of cytotoxic T cell response to various antigens and to certain viral pathogens such as lymphocytic choriomeningitis virus.

In view of the devastating effects that can result from immune disorders, there is a need in the art to provide in vivo systems for screening and evaluating drugs useful in the treatment of these disorders.

Accordingly, it is an object of this invention to provide mammals in which a gene involved in regulation of the immune system has been suppressed through the use of knockout technology.

It is a further object of this invention to provide methods for preparing, and to prepare such knockout mammals.

These and other such objects will readily be apparent to one of ordinary skill in the art.

SUMMARY OF THE INVENTION

In one aspect, the invention provides a mouse and its progeny having a suppressed level of expression of the gene encoding CD28 on T cells. The gene may be suppressed by insertion into the genome of the mouse a nucleic acid sequence comprising at least a portion of an exon of the CD28 coding sequence linked to a marker sequence; the marker sequence can be the neomycin resistance gene.

In another aspect, the invention provides a mouse and its progeny wherein expression of the gene encoding CD45 is suppressed on B cells. The invention further provides mice with a decreased level of CD45 expression on thymocytes and peripheral T cells. Expression of the CD45 gene may be suppressed or decreased by insertion into the genome of the mouse a nucleic acid sequence comprising at least a portion of one exon of CD45 linked to a marker sequence such as the neomycin resistance gene sequence.

In a preferred embodiment, the CD45 gene that is suppressed or decreased is the CD45 exon 6 isoform.

In other aspects, the invention provides embryonic stem cell lines containing a CD28 or a CD45 exon 6 isoform knockout construct.

In yet one other aspect, the invention provides a method of screening a drug for immunostimulatory effects comprising administering the drug to a mouse with a suppressed level of CD28 or CD45 expression, and assaying the mouse for immunostimulation.

DETAILED DESCRIPTION OF THE INVENTION

This invention is based in part on the discovery that the level of expression of a particular gene in a mammal can be decreased or even completely suppressed by introducing into the genomic DNA of the mammal a new DNA sequence that serves to interrupt some portion of the DNA sequence of the gene to be suppressed.

The term "knockout" refers to partial or complete suppression of the expression of at least a portion of a protein encoded by an endogenous DNA sequence in a cell.

The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof.

Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

The terms "CD28" and "CD28 receptor" refer to a cell surface receptor protein that is expressed on certain cells of the immune system, especially T cells. The engagement of CD28 with its ligands B7/BB1, is believed to be an essential co-stimulatory signal necessary for activation of T cells.

The term "CD45", "CD45 receptor" and "L-CA" refer to a cell surface receptor glycoprotein expressed on the surface of many types of hematopoietic cells. CD45 has multiple isoforms ranging in molecular weight from about 180 kD to about 235 kD. Different hematopoietic cell lines express different isoforms of CD45, and some cells may express more than one isoform. As used herein, CD45 refers to any and all of these isoforms.

The term "CD45 exon 6 isoform" refers to the CD45 isoform that expresses exon 6 (as well as other exons) of the CD45 gene. "CD45 exon 6 isoform knockout construct" refers to a knockout construct designed to suppress expression of the CD45 isoform expressing exon 6 (as well as other exons).

The term "marker sequence" refers to a nucleic acid sequence that is (1) used as part of a nucleic acid construct (i.e., the "knockout construct") to disrupt the expression of the gene(s) of interest (such as, for example, CD28 or CD45), and (2) used as a means to identify those cells that have incorporated the knockout construct into the genome. The marker sequence may be any sequence that serves these purposes, although typically it will be a sequence encoding a protein that confers a detectable trait on the cell, such as an antibiotic resistance gene or an assayable enzyme not typically found in the cell. Where the marker sequence encodes a protein, the marker sequence will also typically contain a promoter that regulates its expression.

The terms "rodent" and "rodents" refer to all members of the phylogenetic order Rodentia including any and all progeny of all future generations derived therefrom.

The term "murine" refers to any and all members of the family Muridae, including rats and mice.

The term "progeny" refers to any and all future generations derived and descending from a particular mammal, i.e., a mammal containing a knockout construct inserted into its genomic DNA. Thus, progeny of any successive generation are included herein such that the progeny, the F1, F2, F3, generations and so on indefinitely are included in this definition.

The terms "immunomodulate" and "immunomodulation" refer to changes in the level of activity of any components of the immune system as compared to the average activity of that component for a particular species. Thus, as used herein, immunomodulation refers to an increase or a decrease in activity. Immunomodulation may be detected by assaying the level of B cells, any or all types of T cells, antigen presenting cells, and any other cells believed to be involved in immune function. Additionally or alternatively, immunomodulation may be detected by evaluating 1) the level of expression of particular genes believed to have a role in the immune system, 2) the level of particular compounds such as cytokines (interleukins and the like) or other molecules that have a role in the immune system, and/or 3) the level of particular enzymes, proteins, and the like that are involved in immune system functioning.

Methods of Making the Invention

1, Selection of Knockout Gene(s)

The gene to be knocked out may be any gene provided that at least some sequence information on the DNA to be disrupted is available to use in the preparation of both the knockout construct and the screening probes. Usually, the DNA to be used in the knockout construct will be one or more exon and/or intron regions, and/or a promoter region, but may also be a cDNA sequence provided the cDNA is sufficiently large. Generally, the DNA will be at least about 1 kilobase (kb) in length and preferably 3–4 kb in length, thereby providing sufficient complementary sequence for hybridization when the knockout construct is introduced into the genomic DNA of the ES cell (discussed below). Typically, the gene to be knocked out will be a gene that 1) is expressed in mature and/or immature T cells and/or B cells, 2) is involved, either directly or indirectly, in the activation pathway during inflammation or immunosuppression responses by the immune system, and 3) does not result in lethality when knocked out. Preferred genes to be knocked out are the CD28 and CD45 genes.

Included within the scope of this invention is a mammal in which two or more genes have been knocked out. Such mammals can be generated by repeating the procedures set forth herein for generating each knockout construct, or by breeding to mammals, each with a single gene knocked out, to each other, and screening for those with the double knockout genotype.

The DNA sequence to be used to knock out a selected gene can be obtained using methods well known in the art such as those described by Sambrook et al. (*Molecular Cloning: A Laboratory Manual,* Cold Spring Harbor Laboratory Press, Cold Spring Harbor, N.Y. [1989]). Such methods include, for example, screening a genomic library with a cDNA probe encoding at least a portion of the same gene in order to obtain at least a portion of the genomic sequence. Alternatively, if a cDNA sequence is to be used in a knockout construct, the cDNA may be obtained by screening a cDNA library with oligonucleotide probes or antibodies (where the library is cloned into an expression vector). If a promoter sequence is to be used in the knockout construct, synthetic DNA probes can be designed for screening a genomic library containing the promoter sequence.

Another method for obtaining the DNA to be used in the knockout construct is to manufacture the DNA sequence synthetically, using a DNA synthesizer.

The DNA sequence encoding the knockout construct must be generated in sufficient quantity for genetic manipulation and insertion into ES cells. Amplification may be conducted by 1) placing the sequence into a suitable vector and transforming bacterial or other cells that can rapidly amplify the vector, 2) by PCR amplification, or 3) by synthesis with a DNA synthesizer.

2. Preparation of Knockout Constructs

The DNA sequence to be used in producing the knockout construct is digested with a particular restriction enzyme selected to cut at a location(s) such that a new DNA sequence encoding a marker gene can be inserted in the proper position within this DNA sequence. The proper position for marker gene insertion is that which will serve to prevent expression of the native gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the gene to be suppressed so as to keep the length of the knockout construct comparable to the original genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, however typically it is an antibiotic resistance gene or other gene whose expression or presence in the genome can easily be detected. The marker gene is usually operably linked to its own promoter or to another strong promoter from any source that will be active or can easily be activated in the cell into which it is inserted; however, the marker gene need not have its own promoter attached as it may be transcribed using the promoter of the gene to be suppressed. In addition, the marker gene will normally have a polyA sequence attached to the 3' end of the gene; this sequence serves to terminate transcription of the gene. Preferred marker genes are any antibiotic resistance gene such as neo (the neomycin resistance gene) and beta-gal (beta-galactosidase).

After the genomic DNA sequence has been digested with the appropriate restriction enzymes, the marker gene sequence is ligated into the genomic DNA sequence using methods well known to the skilled artisan and described in Sambrook et al., supra. The ends of the DNA fragments to be ligated must be compatible; this is achieved by either cutting all fragments with enzymes that generate compatible ends, or by blunting the ends prior to ligation. Blunting is done using methods well known in the art, such as for example by the use of Klenow fragment (DNA polymerase I) to fill in sticky ends.

The ligated knockout construct may be inserted directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

3/ Transfection of Embryonic Stem Cells

This invention contemplates production of knockout mammals from any species of rodent, including without limitation, rabbits, rats, hamsters, and mice. Preferred rodents include members of the Muridae family, including rats and mice. Generally, the embryonic stem cells (ES cells) used to produce the knockout mammal will be of the same species as the knockout mammal to be generated. Thus for example, mouse embryonic stem cells will usually be used for generation of knockout mice.

Embryonic stem cells are typically selected for their ability to integrate into and become part of the germ line of a developing embryo so as to create germ line transmission of the knockout construct. Thus, any ES cell line that is believed to have this capability is suitable for use herein.

One mouse strain that is typically used for production of ES cells, is the 129J strain. A preferred ES cell line is murine cell line D3 (American Type Culture Collection catalog no. CRL 1934). The cells are cultured and prepared for DNA insertion using methods well known to the skilled artisan such as those set forth by Robertson (in: *Teratocarcinomas and Embryonic Stem Cells: A Practical Approach*, E. J. Robertson, ed. IRL Press, Washington, D.C. [1987]) and by Bradley et al. (*Current Topics in Devel. Biol.,* 20:357–371 [1986]) and by Hogan et al. (*Manipulating the Mouse Embryo: A Laboratory Manual,* Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

Each knockout construct DNA to be inserted into the cell must first be linearized if the knockout construct has been inserted into a vector. Linearization is accomplished by digesting the DNA with a suitable restriction endonuclease selected to cut only within the vector sequence and not within the knockout construct sequence.

For insertion of the DNA sequence, the knockout construct DNA is added to the ES cells under appropriate conditions for the insertion method chosen. Where more than one construct is to be introduced into the ES cell, DNA encoding each construct can be introduced simultaneously or one at a time.

If the cells are to be electroporated, the ES cells and knockout construct DNA are exposed to an electric pulse using an electroporation machine and following the manufacturer's guidelines for use. After electroporation, the cells are allowed to recover under suitable incubation conditions. The cells are then screened for the presence of the knockout construct.

Screening can be done using a variety of methods. Where the marker gene is an antibiotic resistance gene, the cells are cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Finally, if the marker gene is a gene that encodes an enzyme whose activity can be detected (e.g., beta-galactosidase), the enzyme substrate can be added to the cells under suitable conditions, and the enzymatic activity can be analyzed.

The knockout construct may be integrated into several locations in the ES cell genome, and may integrate into a different location in each cell's genome, due to the occurrence of random insertion events; the desired location of the insertion is in a complementary position to the DNA sequence to be knocked out. Typically, less than about 1–5 percent of the ES cells that take up the knockout construct will actually integrate the knockout construct in the desired location. To identify those cells with proper integration of the knockout construct, the DNA can be extracted from the cells using standard methods such as those described by Sambrook et al., supra. The DNA can then be probed on a Southern blot with a probe or probes designed to hybridize in a specific pattern to genomic DNA digested with (a) particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

4. Injection/Implantation of Embryos

After suitable ES cells containing the knockout construct in the proper location have been identified, the cells are inserted into an embryo. Insertion may be accomplished in a variety of ways, however a preferred method is by microinjection. For microinjection, about 10–30 cells are collected into a micropipet and injected into embryos that are at the proper stage of development to integrate the ES cell into the developing embryo.

The suitable stage of development for the embryo is very species dependent, however for mice it is about 3.5 days. The embryos are obtained by perfusing the uterus of pregnant females. Suitable methods for accomplishing this are known to the skilled artisan, and are set forth by Bradley (in Robertson, ed., supra).

While any embryo of the right age/stage of development is suitable for use, preferred embryos are male and have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo is implanted into the uterus of a pseudopregnant foster mother. While any foster mother may be used, they are typically selected for their ability to breed and reproduce well, and for their ability to care for their young. Such foster mothers are typically prepared by mating with vasectomized males of the same species. The stage of the pseudopregnant foster mother is important for successful implantation, and it is species dependent. For mice, this stage is about 2–3 days pseudopregnant.

5. Screening for Presence of Knockout Gene

Offspring that are born to the foster mother may be screened initially for mosaic coat color where the coat color selection strategy (as described above) has been employed. In addition, or as an alternative, DNA from tail tissue of the offspring may be screened for the presence of the knockout construct using Southern blots and/or PCR as described above. Offspring that appear to be mosaics are then crossed to each other if they are believed to carry the knockout construct in their germ line to generate homozygous knockout animals. If it is unclear whether the offspring will have germ line transmission, they can be crossed with a parental or other strain and the offspring screened for heterozygosity. The heterozygotes are identified by Southern blots and/or PCR amplification of the DNA, as set forth above.

The heterozygotes can then be crossed with each other to generate homozygous knockout offspring. Homozygotes may be identified by Southern blotting of equivalent amounts of genomic DNA from mice that are the product of this cross, as well as mice that are known heterozygotes and wild type mice. Probes to screen the Southern blots can be designed as set forth above.

Other means of identifying and characterizing the knockout offspring are available. For example, Northern blots can be used to probe the mRNA for the presence or absence of transcripts encoding either the gene knocked out, the marker gene, or both. In addition, western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Uses of Knockout Mammals

The mammal of this invention will have a variety of uses depending on the gene or genes that have been suppressed. Where the gene or genes suppressed encode proteins believed to be involved in immunosuppression or inflammation, the mammal may be used to screen for drugs useful for immunomodulation, i.e., drugs that either enhance or inhibit these activities. Screening for useful drugs would involve administering the candidate drug over a range of doses to the mouse, and assaying at various time points for the immunomodulatory effect(s) of the drug on the immune disorder being evaluated. Such assays would include, for example, looking for increased or decreased T and B cell levels, increased or decreased immunoglobulin production, increased or decreased levels of chemical messengers such as cytokines (e.g., interleukins and the like), and/or increased or decreased levels of expression of particular genes involved in the immune response.

For example, patients undergoing chemotherapy often experience immunosuppression. It would be desirable to activate the immune system of such individuals by administering to the patient a therapeutic agent capable of producing such an effect. A mammal of the present invention could be used to screen a variety of compounds, either alone or in combination, to determine whether partial or total restoration or activation of the immune response results.

The same strategy could be applied to find compounds that would be useful in suppressing the inflammatory response observed in many patients with arthritis, or useful in suppressing the autoimmune phenomenon observed in patients with rheumatoid arthritis and lupus.

In addition, mammals of the present invention can be useful for evaluating the development of the immune system, and for studying the effects of particular gene mutations.

Other uses will be readily apparent to one of skill in the art.

The invention will be more fully understood by reference to the following examples. These examples are not to be construed in any way as limiting the scope of this invention.

EXAMPLE I: PREPARATION OF A CD28 KNOCKOUT MOUSE

1. Preparation of Knockout DNA Construct

A genomic clone of the murine CD28 gene (described by Lee et al., *J. Immunol.*, 145:344 [1990]) was isolated from a murine BALB/c genomic library using the murine CD28 exon 2 cDNA sequence as a probe. The 3' end of intron 1 and the 5' region of exon 2 were replaced by inserting a DNA construct encoding the neomycin resistance gene (neo) linked to the herpes simplex virus thymidine kinase promoter. The neo DNA construct was obtained from the plasmid pMCIneoPolA (Thomas et al., *Cell*, 51:503 [1987]) by digestion of this plasmid with restriction endonucleases XbaI and EcoRI. The neo sequence was ligated into the genomic CD28 sequence by cutting the genomic sequence with EcoRI and XbaI, and this neo/CD28 knockout construct was then ligated into the vector pGEM7 (Promega Corp. Madison, Wis.). This vector was transformed into the E. coli bacteria strain DH5 alpha for amplification. After amplification, the plasmid was purified using the standard alkaline lysis and CsCl gradient for purification.

2. Electroporation and Injection of Stem Cells

The purified plasmid knockout construct was linearized by digestion with restriction nuclease AatII thereby generating a shorter arm and a longer arm of CD28 sequence on either side of the neogene. The linearized knockout construct was then transfected into the embryonic stem cell line D3 as follows: About 5 nmol of linearized DNA was added to about $5 \times 10^6$ ES cells in a volume of about 800 µl of culture media. The cells were pulsed at 0.34 kilovolts and 250 µF, and each vial of cells was then plated on to two 10 cm cell culture plates containing embryonic fibroblast feeder cells, and precoated with 1 percent gelatin, and containing 10 ml DMEM medium (Gibco/BRL, Grand Island, N.Y.), 15 percent fetal calf serum (Gibco/BRL, Grand Island, N.Y. or equivalent from Hyclone Labs, Logan, Utah), and leukemia inhibitory factor (Fung-Leung et al. *Cell*, 65:443–449 [1991]). After two days, neo selection was started by adding the antibiotic G418 at 250 µg/ml to the cultures. Cells that survived in the presence of G418 most likely contained the knockout construct. These cells were then screened to verify that the cells that had incorporated the knockout construct in the genomic DNA. Screening was accomplished using the polymerase chain reaction (PCR) method for DNA amplification. Two primers were used in PCR. The first primer was directed to a sequence specific for the thymidine kinase promoter and is set forth below; the second primer, also set forth below, was specific for intron 2 of CD28.

Primer 1 (SEQ ID NO: 1):
5'-CCTGAGTCCTGATCTGTCAGACT-3'
Primer 2 (SEQ ID NO: 2):
5'-ATTCGGCAATGACAAGACGCTGG-3'

The D3 cell line containing the CD28 knockout construct has been deposited with the ATCC (American Type Culture Collection) as accession number CRL11382.

Southern blots of genomic DNA from control and transfected cells were analyzed to assess transfected cells that contained the knockout construct in the proper location and orientation in genomic DNA, (i.e., to identify those cells that had undergone homologous recombination). The Southern blots were probed with two probes. The first probe was a 200 base pair (bp) EcoRI/XbaI fragment of CD28 intron 2. The second probe was a fragment of the neogene and was generated by digesting the plasmid pMC1NeoPolA (described above) with HindIII and XhoI, and isolating the 1.2 kb fragment using standard agarose gel electrophoresis procedures.

Cell lines containing the CD28-neo insert that had inserted into the genomic DNA properly were prepared for injection into murine embryos by trypsin treatment following methods described by Robertson (*Teratocarcinomas and Embryonic Stem Cells: A Practical Approach*, IRL Press, Washington, D.C., [1987], Robertson, E. J., ed). The embryos injected were 3.5 day old embryos obtained by perfusing the uterus of female mice that had been mated with male mice. After injection of the embryonic stem cells into the embryos, the embryos were implanted into pseudopregnant female mice for gestation. The offspring were either mated to each other or with a mouse with suitable coat color so as to be able to detect mice carrying the knockout construct.

3. Screening Mice for Knockout Construct

The offspring of these matings were evaluated for the presence of the knockout construct by probing a Southern blot of DNA obtained from tail tissue with the neogene probe (described above). The probe did not hybridize with DNA obtained from the wild type mice.

To evaluate the level of CD28 expression in knockout and wild type mice, peripheral blood lymphocytes (PBLs) were obtained from these mice by collecting about 25 µl of blood from tail bleeds into a tube containing 100 µl of 20 mM EDTA in phosphate buffered saline (PBS). PBLs were isolated by adding 2 ml of Gey's lysis buffer (to lyse red blood cells) to the blood solution and washing twice with PBS supplemented with 1 percent BSA (bovine serum albumin) and 0.1 percent sodium azide. The cells were incubated with phycoerythrin (PE) conjugated hamster anti-murine CD28 monoclonal antibody (5 µl of a solution of 0.2 mg/ml) obtained from Pharmingen (San Diego, Calif.). The PBLs were then fixed with 1 percent paraformaldehyde. About 5,000 cells were analyzed for each mouse. These cells were then sorted based on PE intensity using FACS (fluorescence activated cell sorting; a Becton-Dickinson [Mountain View, Calif.] FACS machine was used).

4. Analysis of Effects of Knockout Gene

The thymocyte populations of homozygous knockout mice and wild type mice were evaluated for cell surface CD4 and CD8 expression. Thymocytes were stained with FITC-coupled monoclonal antibody directed to CD8, or with phycoerythrin-coupled monoclonal antibody directed to CD4 ( antibodies were obtained from Beckton-Dickinson, Mountain View, Calif.). Splenocytes were evaluated for expression of the cell surface marker B7 and the amount of B cells by staining with FITC-labeled anti B220 and biotin-labeled anti B7 antibody that was detected with PE-labeled streptavidin. The cells were analyzed by FACS, and about 10,000 cells were analyzed for each sample. All mice showed normal CD4/CD8 subtypes in the thymus, suggesting that T cell development was not detectably affected in the knockout mice. In addition, all mice showed a similar B cell and B7 profiles, suggesting that the knockout mice did not compensate for the mutation by altering the level of B7 expression.

Figure 1A:
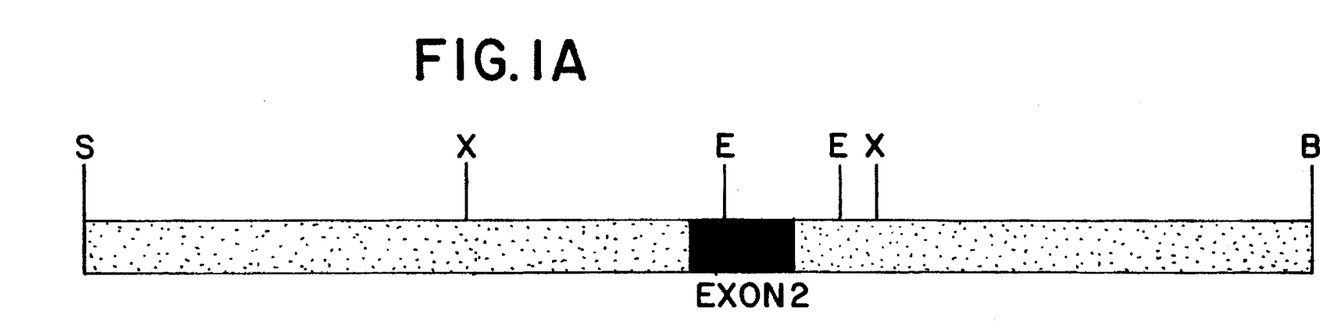
FIGS. 1A, 1B and 1C depicts the knockout construct used to suppress expression of CD28. 1A depicts the structure of a portion of the native CD28 gene. 1B depicts the CD28 knockout construct generated, and 1C depicts this knockout construct inserted into the native CD28 gene after homologous recombination. Restriction enzymes used are indicated by one letter abbreviations. S=SalI; X=XbaI; E=EcoRI; and B=BamHI.
Figure 1B:
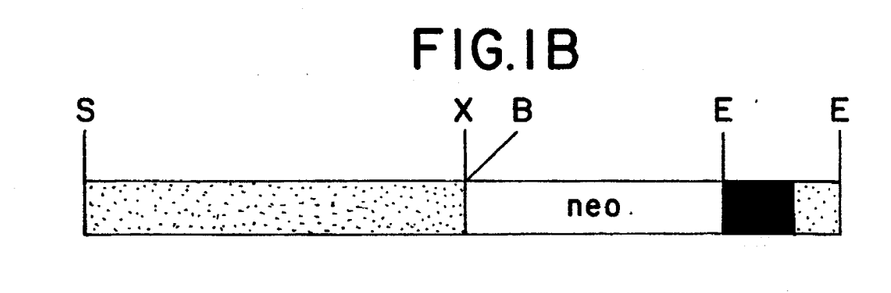
Figure 1C:
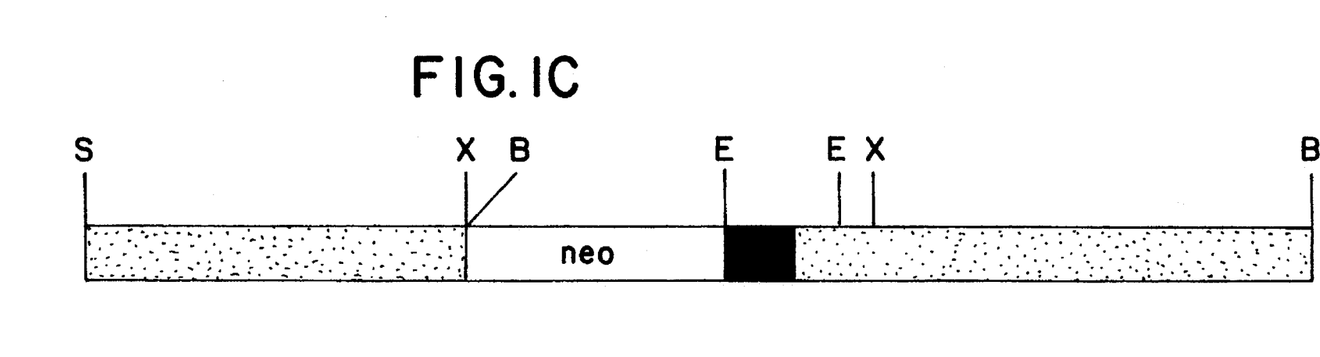
Figure 2:
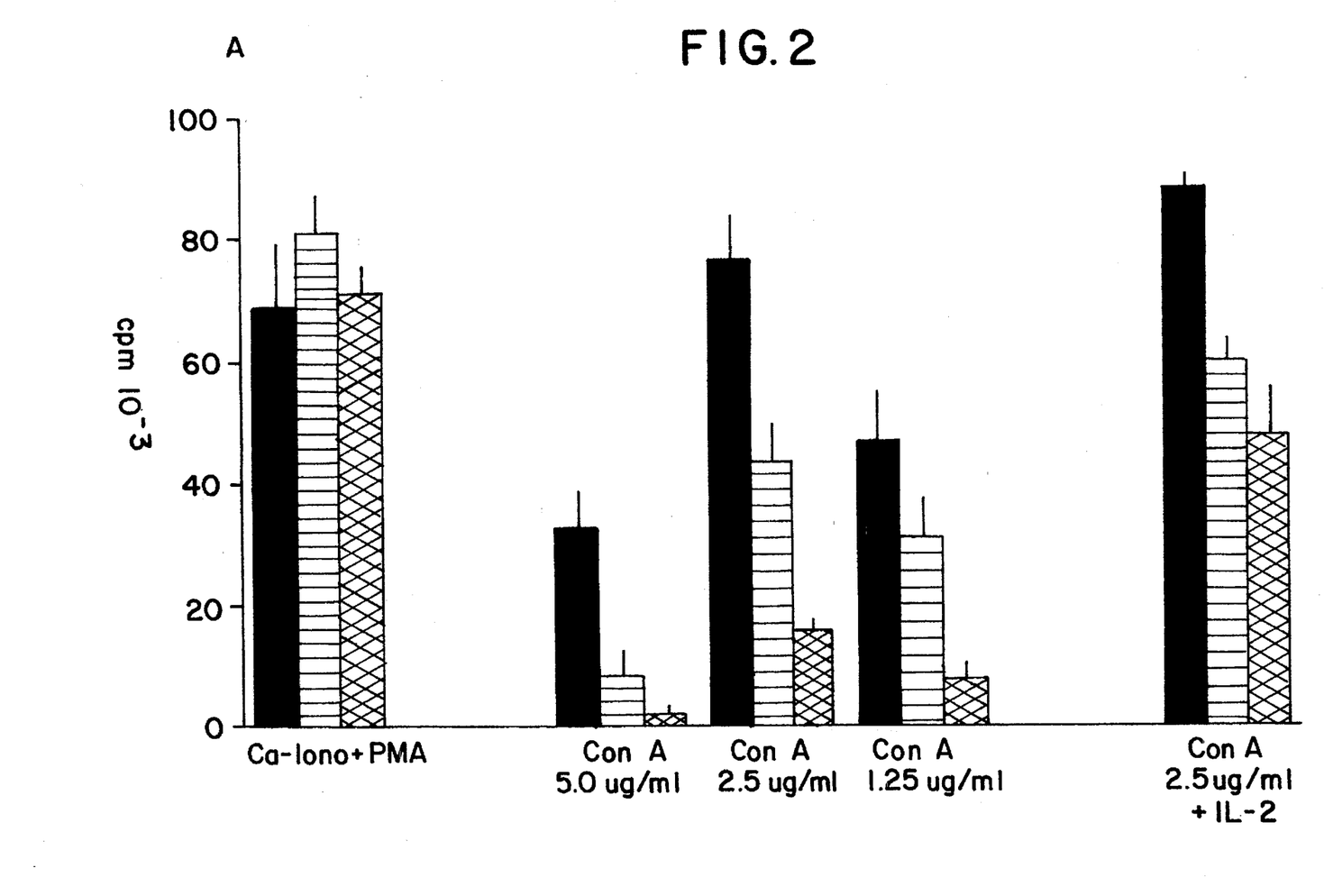
FIG. 2 depicts the effects of the CD28 knockout construct on splenocyte proliferation of 1) the calcium ionophore in combination with PMA, and 2) Concanavalin A (in the presence or absence of IL-2). Solid black bars represent splenocytes from wild type mice, horizontally hatched bars represent splenocytes from heterozygous knockout mice, and cross hatched bars represent splenocytes from homozygous knockout mice. These results were obtained after two days of culturing the cells.

The immune responses of wild type, heterozygous, and homozygous knockout mice were evaluated by assaying splenocytes from each type of mouse for proliferation when exposed to various mitogens. Splenocytes were obtained by sacrificing a mouse and extracting its spleen. The spleen was mashed in media containing 2 percent fetal calf serum, and the red blood cells were lysed as described above. These cells were then plated into 96 well flat bottom plates at a density of about $2 \times 10_5$ cells/well, and various mitogens were added as follows: 1) Concanavalin A (ConA) was evaluated at concentrations between 5.0 µg/ml and 1.25 µg/ml, and at 2.5 µg/ml in either the presence or absence of IL-2; and 2) the calcium ionophore A23167 at 250 ng/ml was evaluated in the presence of the phorbol ester PMA at 50 ng/ml. Cell proliferation was determined by measuring $^3$H-thymidine uptake after two days of culturing. The results are shown in FIG. 2. With respect to ConA, cells from the wild type mice showed a large proliferative response, cells from the heterozygous CD28 knockout mice showed less of a response, and cells from the homozygous CD28 knockout mice had the lowest amount of $^3$H-thymidine uptake. However, the response to the calcium ionophore/PMA was more comparable between the three types of cells.

Figure 3:
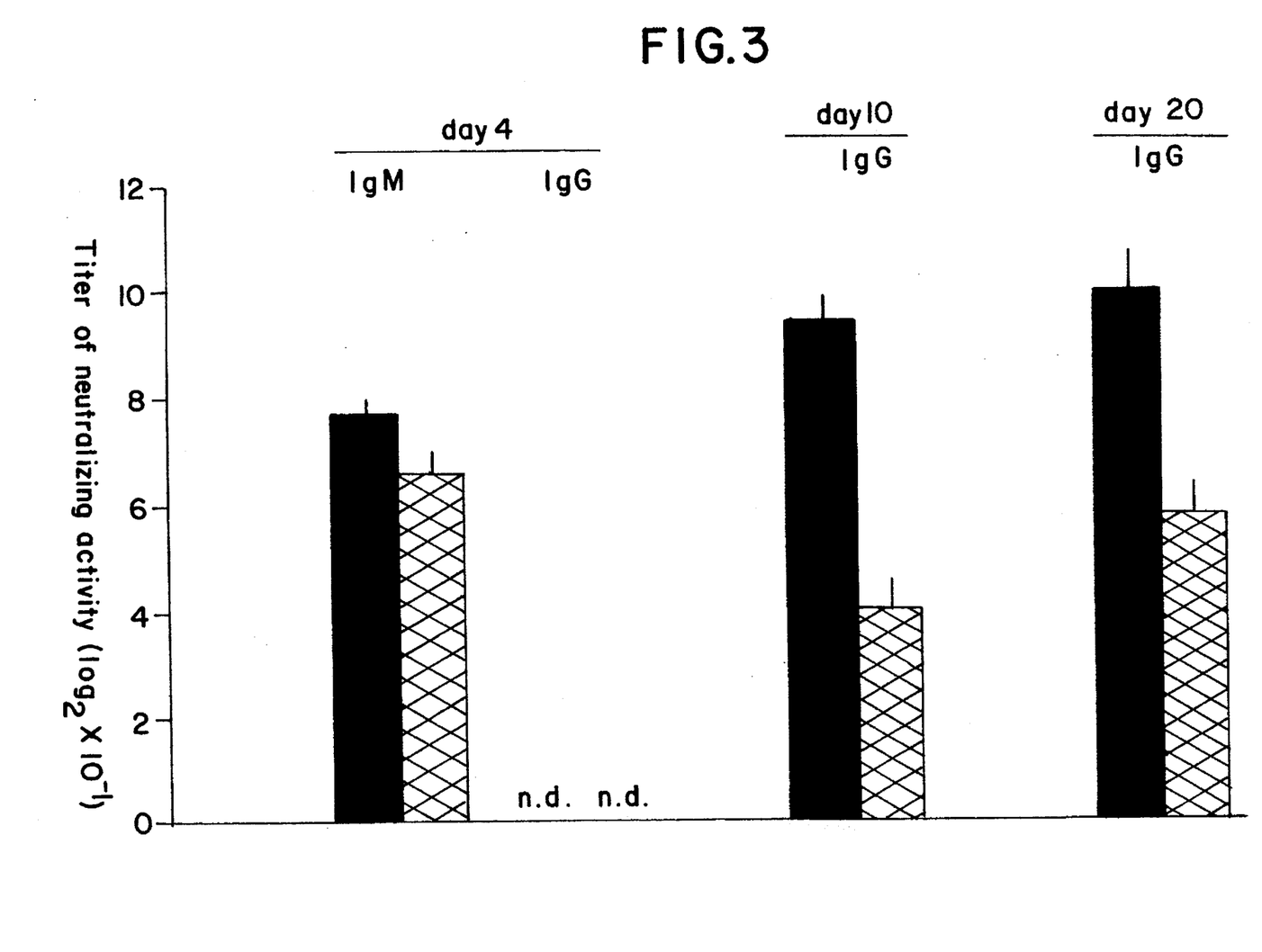
FIG. 3 depicts the level of neutralizing IgM and IgG antibodies in wild type (solid bars) and homozygous CD28 knockout mice (cross hatched bars) immunized with vesicular stomatis virus. Data were collected at various times (as indicated) after immunization. "n.d." indicates no detectable level.

The presence of neutralizing antibodies in the sera in response to infection with vesicular stomatis virus (VSV, Indiana strain) was evaluated. Mice were injected with $2 \times 10^6$ pfu of the virus. After 4, 10, or 20 days, sera from the mice were analyzed for neutralizing IgM and IgG antibodies using methods described by Leist et al. (*J. Immunol.*, 138:2278 [1987]). The results, expressed as titers of neutralizing activity, are shown in FIG. 3. Each bar represents the mean value for a group of 5 mice; n.d. means "not detectable". While titers of homozygous knockout and wild type mice were comparable at day 4, the homozygous knockout mice had much lower levels of IgG than the wild type mice at days 10 and 20.

EXAMPLE 2: PREPARATION OF A CD45 KNOCKOUT MOUSE

1. Preparation of DNA Knockout Construct

Figure 4A:
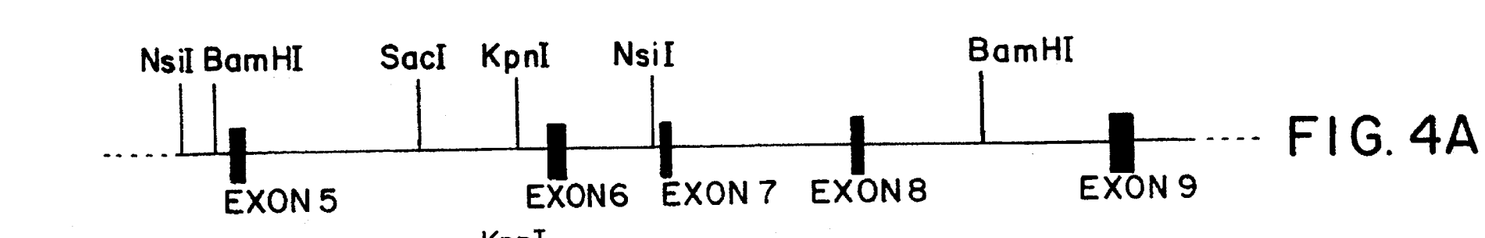
FIGS. 4A, 4B and 4C depicts the DNA knockout construct used to suppress expression of CD45 exon 6 isoform. 4A depicts a portion of the native CD45 gene. 4B depicts the knockout construct where exons 6–8 have been replaced with the neo sequence. 4C shows the restriction sites of the knockout construct.
Figure 4B:
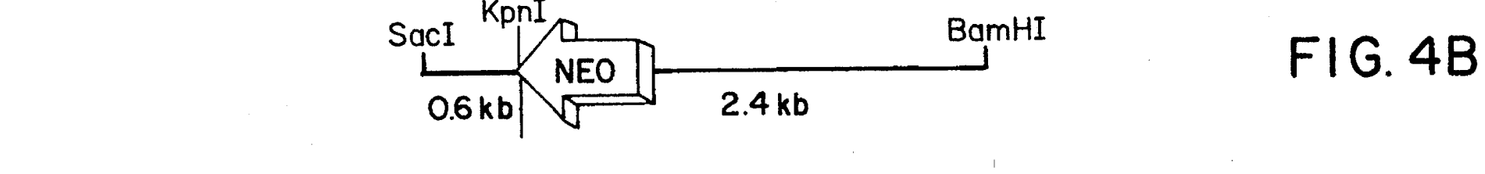
Figure 4C:
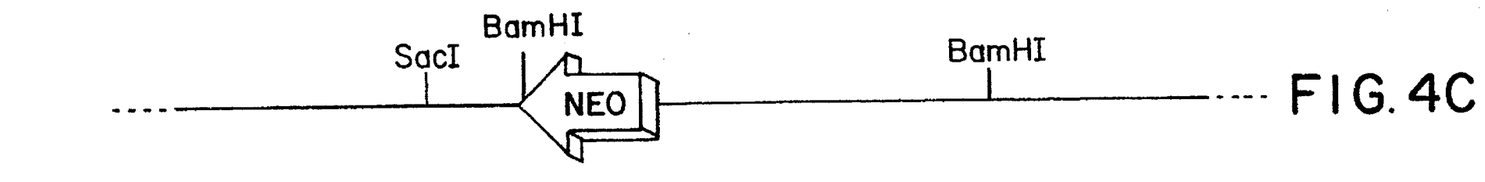

A 4.0 kb genomic murine DNA fragment of the CD45 gene was isolated as described by Johnson et al. (*J. Biol. Chem.*, 264:6220–6229 [1989]) This fragment spans exons 6–8 of the gene. The fragment was inserted into the vector pGEM-9Zf(-) (Promega Corp., Madison, Wis.) previously digested with restriction endonucleases SacI and BamHI. After insertion, the construct was digested with restriction endonucleases KpnI and NsiI; these sites are located between introns 5 and 6, and between introns 6 and 7, respectively of the CD45 gene fragment. The neomycin resistance gene construct containing a poly-A termination signal was obtained from the plasmid pMCIneoPolA (Thomas et al., *Cell*, 51:503 [1987]) and was digested with KpnI and NsiI and was then ligated into the construct in the antisense orientation relative to the CD45 transcriptional orientation. The resulting knockout construct is depicted in FIG. 4.

2. Electroporation and Injection of Stem Cells

The knockout construct was linearized by digestion with restriction endonuclease SacI, and about 25 µg of this DNA was electroporated into D3 embryonic stem cells. The electroporated cells containing the construct have been deposited with the ATCC as accession number CRL11381. Electroporation was accomplished using the procedure described in Example I. About 50 µg DNA per $10^7$ cells was used. After electroporation, the cells were plated and screened as described in Example I.

Cells that were resistant to G418 were screened for homologous recombination by PCR using primers specific for the neomycin resistance gene and for a site specific to the CD45 gene. The primers used are set forth below:

Primer 1 (SEQ ID NO:3)

5'-CTTACTACACATCCCAACCT-3'

Primer 2 (SEQ ID NO:4):

CTTGACGAGTTCTTCTGAGG-3'

PCR reaction conditions were: denaturing at 91° C., annealing at 60° C., and extension at 72° C. About 35–40 cycles were conducted. In addition, homologous recombination in these cells was confirmed by Southern blotting analysis using a $^{32}p$ labeled 1.4 kb DNA probe spanning a region between introns 4 and 5 of the CD45 gene. Southern blotting was conducted by isolating genomic DNA from G418 resistant cells using standard methods as described by Sambrook et al (*Molecular Cloning: A Laboratory Manual*, Cold Spring Harbor Laboratory Press, Cold Spring Harbor, N.Y. [1989]). The genomic DNA was digested with BamHI, separated using standard agarose electrophoresis, and blotted on to Immobilon-N membrane paper. Transfer to the membrane was done at 20° C. for 12 hours in 10 percent SSC (Sambrook et al., supra). The membrane was probed for 12 hours at 67° C., and then washed three times. The first wash was 5 percent SSC, 0.01 percent SDS; the second wash was 3 percent SSC, 0.01 percent SDS; the third wash was 1 percent SSC, 0.01 percent SDS.

Preparation of ES cells, injection into embryos, and implantation into foster mothers was as described in Example I. 3. Screening Mice for Knockout Construct Offspring (the founder mice) were screened for mosaicism by evaluating fur pigmentation (the embryo was from a black fur mouse and the embryonic stem cell was from an agouti mouse; most mosaic mice therefore had a coat that was partially agouti and partially black). The founder mice were back crossed to generate heterozygous CD45 knockout mice. Offspring from this cross were screened to determine whether they were heterozygous or homozygous for the CD45 knockout construct. Screening was done by Southern blotting of DNA obtained from tail tissue. The tail tissue was obtained by cutting off a piece of the tail of 3 week old mice. The tail tissue was incubated with 500 µl of a solution of TNE (Sambrook et al., supra), 150 µg/ml Proteinase K, 1 percent SDS, and 1 mg/ml Pronase E. After this incubation, 750 µl of this solution was added to 750 µl of phenol:chloroform (1:1 v/v) to isolate the DNA. The mixture was centrifuged 5 minutes to pellet cellular debris. The supernatant was added to 450 µl of isopropyl alcohol and this mixture was incubated on dry ice to precipitate the DNA. After incubation, the precipitated DNA was pelleted by centrifugation, air dried, and resuspended in 100 µl of distilled water, and kept at 4° C. Southern blots of this DNA were done as describe above for the embryonic stem cells.

To test the B cells and T cells of the mice for expression of CD45 and to determine the zygosity of the mice, cells from various mice were screened for the presence of immunological markers using antibodies and methods as described below.

Single cell suspensions of thymocytes, splenocytes, mesenteric lymph node cells and bone marrow cells from 6–12 week old mice were prepared as follows: Mice were sacrificed using carbon dioxide following standard protocols of the Canadian Research Council, and organs were harvested from each mouse and kept in phosphate buffered saline (PBS) at 4° C. Single cell suspensions were prepared by grinding the organs against a steel screen mesh with a syringe plunger. The cells were washed twice in PBS. Each suspension was resuspended in PBS and incubated with the appropriate antibodies as follows:

1) Pan-CD45 antigen was detected with either 1) FITC (fluorescein isothiocyanate) or PE (phycoerythrin) labeled Ly-5 monoclonal antibody (Pharmingen, San Diego, Calif.) or 2) with rat the IgG monoclonal antibody 13/2.3 derived from supernatant (Trowbridge et al., *J. Exp. Med.*, 148:313 [1978]).

2) The CD45-exon 4 encoded epitope was detected with rat monoclonal antibody 14.8 derived from supernatant; obtained from Kincade et al., *J. Immunol.*, 127:2262–2268 [1981]).

3) The CD45-exon 5 encoded epitope was detected with rat IgG monoclonal antibody MB23G2 obtained from supernatant (Birkeland et al., *Proc. Natl. Acad. Sci. USA*, 86:6734–6738 [1989]).

4) A CD45 glycosylation epitope of B cells was detected with monoclonal antibody B220 (FITC or PE labeled; Pharmingen, San Diego, Calif.).

5) CD4 was detected with anti-CD4 monoclonal antibody (FITC or PE labeled) obtained from Becton-Dickinson (Mountain View, Calif.).

6) CD8 was detected with anti-CD8 monoclonal antibody (FITC, PE, or biotin labeled) obtained from Becton-Dickinson (Mountain View, Calif.).

7) TCRVbeta8.1+8.2 was detected with KJ16 rat IgG monoclonal antibody (Hoskins et al., *J. Exp. Med.*, 160:452–471 [1984]).

8) TCRVbeta8.2 was detected with mouse IgG monoclonal antibody F23.2 (Staerz et al., *J. Immunol.* 134:3994–4000 [1985]).

9) H-2b was detected with FITC labeled monoclonal antibody B8-24 (Pharmingen, San Diego, Calif.).

10) H-2d was detected with FITC labeled monoclonal antibody 34-2-12 (Pharmingen, San Diego, Calif.)

11) CD3 was detected with anti-CD3 monoclonal antibody (Pharmingen, San Diego, Calif.).

12) Thy1.2 was detected with anti-Thy1.2 FITC or PE labeled monoclonal antibody (Pharmingen, San Diego, Calif.).

13) sIgM antigen was detected with FITC labeled monoclonal antibody (Pharmingen, San Diego, Calif.).

Labeling the cells with the antibodies was performed as follows: For single or double staining using PE or FITC labeled antibody, about $1 \times 10^6$ cells were incubated with 4 µl of labeled antibody at 4° C. for 30 minutes in 100 µl of a solution of Staining Buffer consisting of PBS with 10 percent fetal calf serum (FCS) and 0.1 percent sodium azide. The cells were then washed once in 5 ml PBS and fixed in 1 percent paraformaldehyde (in PBS) and kept at 4° C. until ready for FACS analysis.

For labeling cells using the supernatants, $1 \times 10^6$ cells were incubated with about 50 µl of the appropriate supernatant for 30 minutes at 4° C. in 100 µl Staining Buffer. After this incubation, antibody binding was visualized by incubation with 3 µl of PE or FITC labeled goat anti-mouse IgG, or goat anti-rabbit IgG (both obtained from Southern Biotechnology Associates, Birmingham, Ala.) for 30 minutes at 4° C. The cells were then washed once in PBS and then fixed in paraformaldehyde as described above.

Visualization of rat or mouse antibodies was conducted using PE or FITC labeled goat anti-rat IgG and FITC labeled goat anti-mouse antisera (both obtained from Southern Biotechnology Associates, Birmingham, Ala.), and visualization of biotin labeled antibodies was with streptavidin-RED613 (Gibco/BRL, Grand Island, N.Y.). Where double staining protocols with rat antibodies were used, unspecific staining due to remaining anti-rat IgG sites was first blocked using 2 µg/100 µl rat IgG (Sigma Chemical Co., St. Louis, Mo.) and incubating the cells at 4° C. for 10 minutes before washing with PBS. All samples were analyzed with a FACScan machine using a Lysis II program (Becton-Dickinson, Mountain View, Calif.)

The results demonstrated that CD45 exon 6 isoform was not detected on the cell surface of B lymphocytes from bone marrow and spleen of homozygous CD45 exon 6 isoform knockout mice. In addition, the number of peripheral T cells that expressed CD45 exon 6 isoform on the cell surface was significantly reduced as compared with wild type mice. Heterozygous knockout mice had a decreased level of CD45 exon 6 isoform expression on these cells as compared to wild type mice.

The total number of sIgM+ cells in the spleen and bone marrow was comparable between homozygous knockout mice and wild type mice. However, the total number of T cells in peripheral lymphoid organs was considerably reduced in the homozygous knockout mice as compared to wild type mice. No significant differences in peripheral T and B cell compartments and bone marrow cells were detected between heterozygous knockout mice and wild type mice even though CD45 was expressed at a reduced level in heterozygous knockout mice as compared to wild type mice.

Although CD45 exon 6 isoform expression on thymocytes was significantly suppressed in homozygous knockout mice as compared to wild type mice, the total number of thymocytes in homozygous knockout mice was only slightly reduced as compared to wild type mice. In addition, homozygous knockout mice had normal numbers of immature CD4+ CD8+ double positive thymocytes, however, the total number of CD4– CD8– precursor cells was increased, and the size of both mature CD4+ and CD8+ T cell lineages was significantly reduced in these mice.

4. Analysis of Effects of Knockout Gene

To examine the effects of CD45 exon 6 isoform gene suppression on B cell development, single cell suspensions of bone marrow, spleen, or peritoneum cells were cloned in semi-solid agar under a variety of conditions that allow selective proliferation of either pre-B cells (IL-7 or IL-7 plus the stroma cell line S17), B cells (LPS or LPS+S17) or myeloid cells (IL-3 or L929 conditioned medium as a source of macrophage colony stimulating factor M-CSF-1). To evaluate proliferation, double layer agar cultures were established as follows: first, a 1 ml underlayer consisting of OPTI-MEM medium (Gibco/BRL, Grand Island, New York) supplemented with 2.4 g/l NaHCO$_3$, 5 mg/l streptomycin, $5 \times 10^3$ u/l penicillin, $5 \times 10^{-5 M}$ beta-mercaptoethanol, 10% fetal calf serum (Gibco/BRL, Grand Island, New York) and 0.3% melted Bacto agar (Difco Labs) was prepared. Next, the S17 stromal cells (Collins et al., *J. Immunol* 138: 1082–1087 [1987]) were allowed to adhere to the plastic plate for 5 hours ($2 \times 10^4$ irradiated [2000Gy] S17/plate). Nonadherent cells were then removed by vacuum suction, and the bottom agar layer containing the appropriate supplements was poured.

The media was supplemented with either LPS at 25 µg/ml (lipopolysaccharide from *Salmonella typhosa* strain WO901; Difco Labs); murine IL-7 and IL-3 (added to the media as culture supernatants from cell lines containing the appropriate vectors; described in detail by Cumano et al., *Eur. J. Immunol.*, 20:2183–2189 [1990]; Cumano et al., *EMBO J.*, 11:593–601 [1992]; Karasuyama et al., *Eur J. Immunol.* 18:97–104 [1988]); or macrophage-colony stimulating factor (M-CSF-1; obtained from L929 conditioned medium). Optional amounts of IL-3, IL-7 and M-CSF were determined in titration experiments as described by Cumano et al., supra.

The results are shown in Table I as the absolute numbers of colony forming cells found in different tissues tested. There was no detectable difference in the amount of colony formation of bone marrow derived myeloid or B-cell progenitors between homozygous knockouts, heterozygous knockouts and wild type mice.

| Total Number of Lymphoid Cells ($\times 10^8$) | | | |
|---|---|---|---|
| Lymphatic Organ | Wild-type | Heterozygotes | Homozygotes |
| Thymus | 1.20 (0.27) | 1.10 (0.15) | 0.76 (0.14) |
| Thymus + DXT | 0.15 (0.05) | 0.16 (0.05) | 0.03 (0.01) |
| Spleen | 0.78 (0.11) | 0.93 (0.29) | 1.96 (0.38) |
| Lymph Nodes | 0.31 (0.03) | 0.33 (0.09) | 0.41 (0.07) |
| Bone Marrow | 0.46 (0.06) | 0.38 (0.09) | 0.35 (0.09) |
| Blood Leukocytes ($\times 10^6$)/ml | 7.7 (0.3) | 8.1 (1.2) | 7.4 (1.8) |

(Numbers in parentheses refer to standard deviation)

To determine the importance of CD45 exon 6 isoform expression on immunoglobulin (Ig) mediated cell signaling effects, the anti-Igµ specific monoclonal antibody B-76 (obtained from Dr. Michael Julius, McGill University, Montreal, Canada) was added to splenic B cells obtained from homozygous and heterozygous knockout mice as well as wild type mice. Splenic B cells were placed in microtiter plates at a density of about $10^5$ cells/well and incubated for 3, 4, or 5 days in an atmosphere of 5 percent $CO_2$ at 37° C. with either no exogenous stimulant added, or lipopolysaccharide or antibody B-76 added. Stimulation was measured by adding $^3$H-thymidine to the cells for 10 hours using 1 μCi of $^3$H-thymidine per well. The contents of each well was then blotted on to filter paper and counted for radioactivity.

Figure 5A:
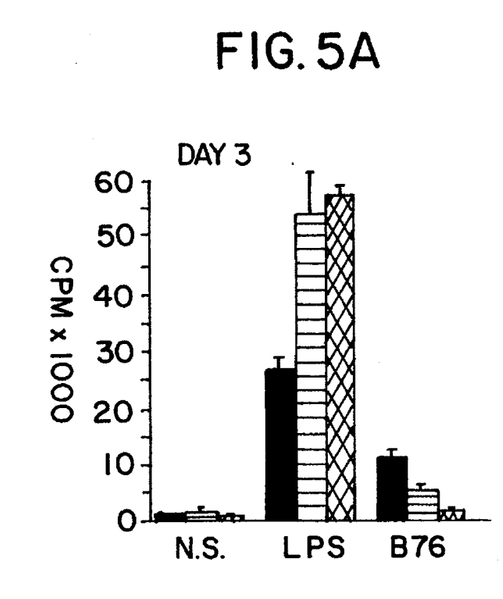
FIG. 5 depicts the proliferation of splenocytes from wild type (solid bars), heterozygous CD45 knockout (single hatched bars) or homozygous CD45 knockout (double hatched bars) mice in response to either 1) lipopolysaccharide (LPS), or 2) purified anti-μ antibodies (B-7-6). These data were obtained 3, 4, Or 5 days after the stimulants were added to the culture media. "N.S." indicates no stimulant added.
Figure 5B:
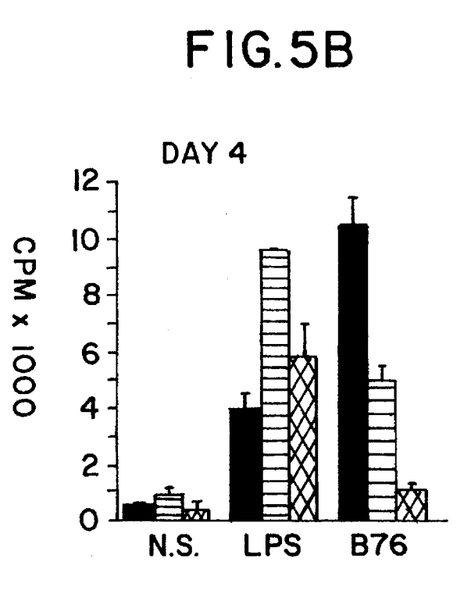
Figure 5C:
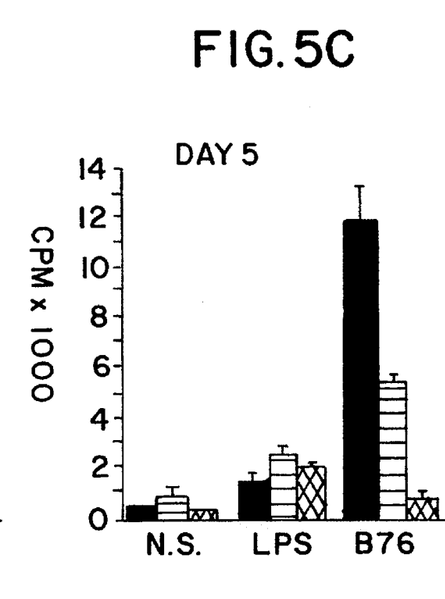

The results, shown in FIG. 5, indicated that anti-Igμ stimulation requires CD45 exon 6 isoform expression on B cells whereas LPS stimulation does not.

Figure 6A:
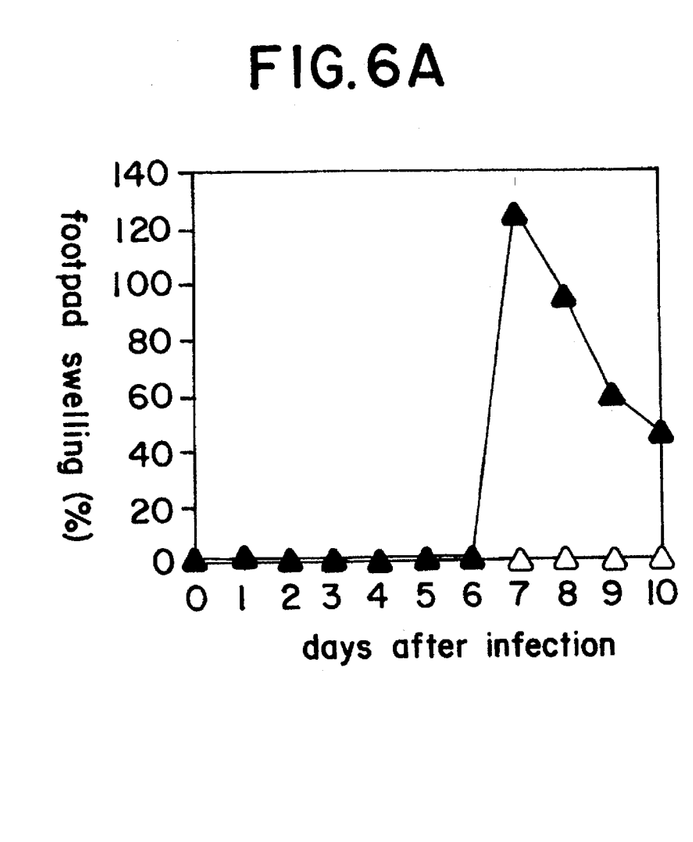
FIGS. 6A and 6B depicts the cytotoxic T cell response of wild type and CD45 exon 6 isoform homozygous knockout mice when exposed to LCMV (lymphocytic choriomeningitis virus strain Armstrong). 6A depicts the footpad swelling reaction, and 6b depicts specific lysis of LCMV infected cells. Open triangles represent the homozygous CD45 exon 6 isoform knockout mice, and closed triangles represent the wild type mice.

To evaluate T cell effector functions in vivo, homozygous and heterozygous knockout mice were tested for their ability to generate an antiviral cytotoxic T cell response. About 30 μl of lymphocytic choriomeningitis virus Armstrong (LCMV) equivalent to about 400 pfu was injected subcutaneously into the hind footpads of the mice. Swelling of the footpad was measured daily with a spring loaded caliper. The results are shown in FIG. 6A. The early phase of the swelling reaction (days 7–9 after infection) was completely abrogated in homozygous knockout mice (open triangles) but not in wild-type mice (closed triangles).

To further confirm the inability of homozygous knockout mice to generate a cytotoxic response to certain pathogens, cytotoxic lymphocytes were obtained from spleens of mice after the mice had been infected with LCMV. These cytotoxic lymphocytes were then restimulated in vitro 5 or 30 days after the initial infection. Restimulation was accomplished by exposure to LCMV infected peritoneal macrophages (Lehmann-Grube, *Virol. Monogr.*, 10 [1971]) prepared as follows: macrophages were obtained by washing the peritoneum of C57BL/6 mice which had been injected six days earlier with 2 ml of thioglycolic acid (3 percent wt/vol.) and were infected intraperitoneally four days earlier with 1000 pfu LCMV Armstrong.

Cultures were established with $4 \times 10^6$ responder spleen cells and $2 \times 10^5$ LCMV infected irradiated (1200 rads) peritoneal macrophages. The cultures were incubated for 5 days in IMDM medium with 10 percent fetal calf serum and $10^{-5}$ M beta-mercaptoethanol. Duplicate dilutions of the cultures were assayed for LCMV specific T cell cytotoxicity on LCMV infected $^{51}$Cr labeled MC57(H-2b) fibrosarcoma target cells according to standard protocols described by Cerrottini et al. (*Adv. Immunol.*, 18:67–132 [1974]). Specific lysis after four hours was then calculated as described by Cerrottini et al., supra.

Figure 6B:
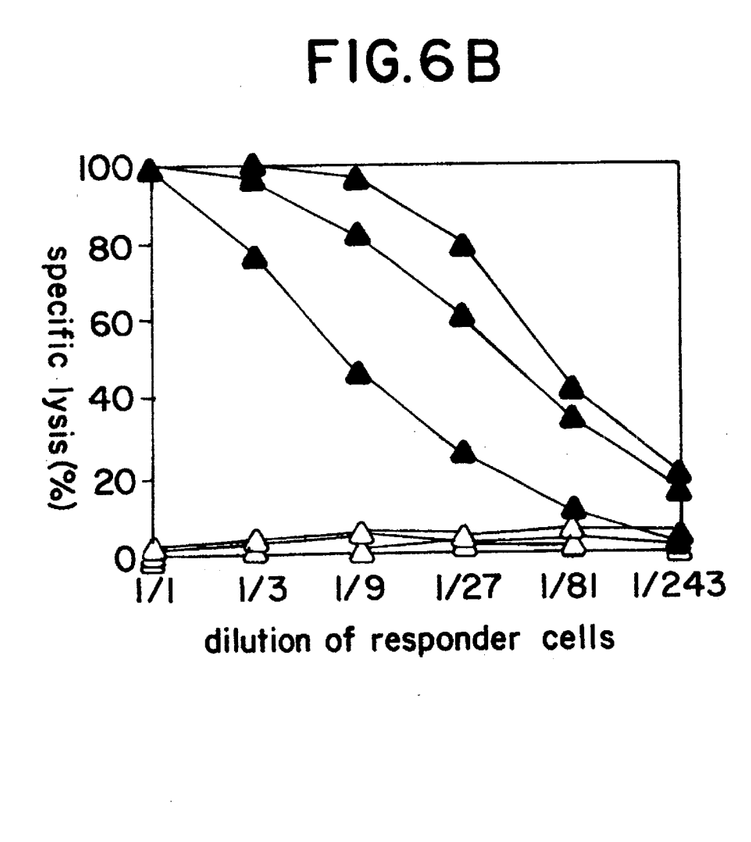

The results, shown in FIG. 6B, indicate that homozygous knockout mice (open triangles) were unable to mount a cytotoxic response, while wild-type mice (closed triangles) were able to mount such a response.

All literature cited herein is specifically incorporated by reference.

---

---

We claim:

1. A DNA construct comprising intron 1 and exon 2 of a mouse CD28 gene into which a marker sequence has been inserted.

2. The DNA construct of claim 1 wherein said marker sequence comprising a neogene operably linked to a thymidine kinase promoter is substituted for the region between the XbaI site in intron 1 and the EcoRI site in exon 2 of the CD28 gene.

3. A mouse D3 embryonic stem cell line comprising the DNA construct of claim 2 and having the ATCC accession number CRL11382.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 23 base pairs
        ( B ) TYPE: Nucleic Acid
        ( C ) STRANDEDNESS: Single stranded
        ( D ) TOPOLOGY: Linear     ( x i ) SEQUENCE DESCRIPTION: SEQ ID NO:1:

CCTGAGTCCT GATCTGTCAG ACT      23

( 2 ) INFORMATION FOR SEQ ID NO:2:

( i ) SEQUENCE CHARACTERISTICS:
        ( A ) LENGTH: 23 Base pairs
        ( B ) TYPE: Nucleic acid
        ( C ) STRANDEDNESS:Single stranded
        ( D ) TOPOLOGY: Linear     ( x i ) SEQUENCE DESCRIPTION: SEQ ID NO:2:

ATTCGGCAAT GACAAGACGC TGG      23

( 2 ) INFORMATION FOR SEQ ID NO:3:

( i ) SEQUENCE CHARACTERISTICS:
        ( A ) LENGTH: 20 Base pairs
        ( B ) TYPE: Nucleic acid
        ( C ) STRANDEDNESS: Single stranded
        ( D ) TOPOLOGY: Linear     ( x i ) SEQUENCE DESCRIPTION: SEQ ID NO:3:

CTTACTACAC ATCCCAACCT      20

( 2 ) INFORMATION FOR SEQ ID NO:4:

( i ) SEQUENCE CHARACTERISTICS:
        ( A ) LENGTH: 20 Base pairs
        ( B ) TYPE: Nucleic acid
        ( C ) STRANDEDNESS: Single stranded
        ( D ) TOPOLOGY: Linear     ( x i ) SEQUENCE DESCRIPTION: SEQ ID NO:4:

CTTGACGAGT TCTTCTGAGG     20